US011795554B2

(12) United States Patent
Rabindran et al.

(10) Patent No.: US 11,795,554 B2
(45) Date of Patent: Oct. 24, 2023

(54) METHOD OF PRODUCING ISOPROPANOL FROM ELECTROCHEMICAL REDUCTION OF CARBON DIOXIDE AND RELATED COPPER-BASED ELECTROCATALYSTS

(71) Applicant: Research Triangle Institute, Research Triangle Park, NC (US)

(72) Inventors: Aravind Villava Rayer Rabindran, Morrisville, NC (US); Elliot Reid, Atlanta, GA (US); Ignacio Luz Minguez, Durham, NC (US); Mustapha Soukri, Cary, NC (US); Marty Lail, Raleigh, NC (US); Shaojun James Zhou, Cary, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 109 days.

(21) Appl. No.: 16/786,150

(22) Filed: Feb. 10, 2020

(65) Prior Publication Data

US 2020/0255961 A1 Aug. 13, 2020

Related U.S. Application Data

(60) Provisional application No. 62/804,404, filed on Feb. 12, 2019.

(51) Int. Cl.
*C25B 3/07* (2021.01)
*C25B 3/26* (2021.01)
(Continued)

(52) U.S. Cl.
CPC ............. *C25B 3/25* (2021.01); *B01J 31/1616* (2013.01); *B01J 37/08* (2013.01); *C09D 11/52* (2013.01);
(Continued)

(58) Field of Classification Search
CPC ................ C25B 3/07; C25B 3/25; C25B 3/26
(Continued)

(56) References Cited

U.S. PATENT DOCUMENTS

| 2009/0014336 A1* | 1/2009 | Olah | C25B 15/08 205/450 |
| 2018/0119296 A1* | 5/2018 | Geioushy | C25B 3/25 |

(Continued)

FOREIGN PATENT DOCUMENTS

KR 101750279 B1 * 6/2017 ............... C25B 3/04

OTHER PUBLICATIONS

Goncalves et al., "Electrochemical Conversion of CO2 to C2 Hydrocarbons Using Different Ex Situ Copper Electrodeposits," Electrochimica Acta (Jul. 15, 2013), vol. 102, pp. 388-392. (Year: 2013).*

(Continued)

*Primary Examiner* — Edna Wong
(74) *Attorney, Agent, or Firm* — NK Patent Law (57) ABSTRACT

A carbon dioxide reduction reaction electrocatalyst comprises a pyrolyzed copper-based metal-organic framework (MOF) that produces isopropanol from electrochemical reduction of carbon dioxide. A process for producing isopropanol from electrochemical reduction of carbon dioxide comprises applying a potential in an electrochemical cell in the range of about −2V to about −3V versus a silver chloride electrode.

19 Claims, 10 Drawing Sheets

(51) Int. Cl.
| | |
|---|---|
| C25B 3/25 | (2021.01) |
| B01J 31/16 | (2006.01) |
| B01J 37/08 | (2006.01) |
| C09D 11/52 | (2014.01) |
| C25B 11/043 | (2021.01) |
| C07C 31/10 | (2006.01) |
| C25B 15/08 | (2006.01) |

(52) U.S. Cl.
CPC ......... *C25B 11/043* (2021.01); *B01J 2531/16* (2013.01); *C07C 31/10* (2013.01); *C25B 15/08* (2013.01)

(58) Field of Classification Search
USPC .......................................................... 205/450
See application file for complete search history.

(56) References Cited

U.S. PATENT DOCUMENTS

| | | | | |
|---|---|---|---|---|
| 2018/0219240 | A1* | 8/2018 | Gyenge | H01M 8/20 |
| 2019/0067706 | A1* | 2/2019 | Liu | C25B 11/095 |
| 2019/0186027 | A1* | 6/2019 | Kirk | C25B 15/02 |
| 2021/0123146 | A1* | 4/2021 | Berlinguette | B01D 53/965 |

OTHER PUBLICATIONS

Yano et al., "Selective Electrochemical Reduction of CO2 to Ethylene at a Three-Phase Interface on Copper(I) Halide-Confined Cu-Mesh Electrodes in Acidic Solutions of Potassium Halides," Journal of Electroanalytical Chemistry (Apr. 15, 2004), vol. 565, No. 2, pp. 287-293. (Year: 2004).*
Shaklein, "Electrochemical Characterisation of Bimetallic Materials for CO2 Reduction," 2017, pp. 1-30. (Year: 2017).*
Perfecto-Irigaray et al., "Synthesis of Heterometallic Metal-Organic Frameworks and Their Performance as Electrocatalyst for CO2 Reduction," RSC Advances (2018), vol. 8, No. 38, pp. 21092-21099. (Year: 2018).*
Al-Rowaili et al., "A Review on Recent Advances for Electrochemical Reduction of Carbon Dioxide to Methanol Using Metal-Organic Framework (MOF) and Non-MOF Catalysts: Challenges and Future Prospects," ACS Sustainable Chemistry & Engineering (Oct. 24, 2018), vol. 6, No. 12, pp. 15895-15914. (Year: 2018).*
Albo et al., "Copper-Based Metal-Organic Porous Materials for CO2 Electrocatalytic Reduction to Alcohols," ChemSusChem. (Mar. 22, 2017), vol. 10, No. 6, pp. 1100-1109. (Year: 2017).*
Zhao et al., "CO2 Electroreduction at Low Overpotential on Oxide-Derived Cu/Carbons Fabricated From Metal Organic Framework," ACS Applied Materials & Interfaces (Feb. 15, 2017), vol. 9, No. 6, pp. 5302-5311. (Year: 2017).*
Wang et al., "Metal-Organic-Framework-Mediated Nitrogen-Doped Carbon for CO2 Electrochemical Reduction," ACS Applied Materials & Interfaces (Apr. 11, 2018), vol. 10, No. 17, pp. 14751-14758. (Year: 2018).*
Qiu et al., "Selective Electrochemical Reduction of Carbon Dioxide Using Cu Based Metal Organic Framework for CO2 Capture," ACS Applied Materials & Interfaces (Jan. 24, 2018), vol. 10, No. 3, pp. 2480-2489. (Year: 2018).*
Ellison et al., Mass Transfer to a Rotating Disk, Journal of the Electrochemical Society (1971), vol. 118, No. 1, pp. 68-69. (Year: 1971).*
Kumar et al., "Highly Selective Electrochemical Reduction of Carbon Dioxide Using Cu Based Metal Organic Framework as an Electrocatalyst," Electrochemistry Communications (Nov. 1, 2012), vol. 25, pp. 70-73. (Year: 2012).*
G.M. Woodwell, The Carbon Dioxide Question, Scientific American 238(1) (1978) 34-43.
U.S. Department of Commerce, National Oceanic and Atmospheric Administration, in: E.S.R. Laboratory (Ed.) 2018.
Jessop, Philip G., "Review of Greenhouse Gas Carbon Dioxide Mitigation: Science and Technology by Martin M. Halmann". J.Am. Chem. Soc., vol. 123, No. 29, 2001.
I. Dimitriou, P. García-Gutiérrez, R.H. Elder, R.M. Cuéllar-Franca, A. Azapagic, R.W.K. Allen, Carbon dioxide utilisation for production of transport fuels: process and economic analysis, Energy & Environmental Science 8(6) (2015) 1775-1789.
J. Albo, M. Alvarez-Guerra, P. Castaño, A. Irabien, Towards the electrochemical conversion of carbon dioxide into methanol, Green Chemistry 17(4) (2015) 2304-2324.
D.T. Whipple, P.J.A. Kenis, Prospects of CO2 Utilization via Direct Heterogeneous Electrochemical Reduction, the Journal of Physical Chemistry Letters 1(24) (2010) 3451-3458.
D.R. Kauffman, J. Thakkar, R. Siva, C. Matranga, P.R. Ohodnicki, C. Zeng, R. Jin, Efficient Electrochemical CO2 Conversion Powered by Renewable Energy, ACS Applied Materials & Interfaces 7(28) (2015) 15626-15632.
Summary of Report-IT, Industrial Alcohol Market Analysis, by Product (Ethyl Alcohol, Methyl Alcohol, Isopropyl Alcohol, Isobutyl Alcohol), by Source, by Application, by Region, and Segment Forecasts, 2018-2025, Market Research Report-Report ID: GVR-2-68038-236-5, 2017.
Summary of R. Gimr, Industrial Alcohol Market Analysis 2018—Growth by Companies, Trends by Types and Application, Forecast Analysis to 2023 Industrial Alcohol Market Research Report Forecast to 2023-Report ID: MRFR/CnM/4331-HCRR 2018.
K.P. Kuhl, E.R. Cave, D.N. Abram, T.F. Jaramillo, New insights into the electrochemical reduction of carbon dioxide on metallic copper surfaces, Energy & Environmental Science 5(5) (2012) 7050-7059.
Y. Hori, A. Murata, R. Takahashi, Formation of hydrocarbons in the electrochemical reduction of carbon dioxide at a copper electrode in aqueous solution, Journal of the Chemical Society, Faraday Transactions 1: Physical Chemistry in Condensed Phases 85(8) (1989) 2309-2326.
J. Qiao, Y. Liu, F. Hong, J. Zhang, A review of catalysts for the electroreduction of carbon dioxide to produce low-carbon fuels, Chemical Society Reviews 43(2) (2014) 631-675.
M. Schwartz, Cook, R.L., Kehoe, V.M., MacDuff, R. C., Patel, J., Sammells, A. F., Carbon Dioxide Reduction to Alcohols using Perovskite-Type Electrocatalysts, Journal of Electrochemical Society 140(3) (1993) 614-618.
A. Loiudice, P. Lobaccaro, E.A. Kamali, T. Thao, B.H. Huang, J.W. Ager, R. Buonsanti, Tailoring Copper Nanocrystals towards C2 Products in Electrochemical CO2 Reduction, Angewandte Chemie International Edition 55(19) (2016) 5789-5792.
S. Munir, A.R. Varzeghani, S. Kaya, Electrocatalytic reduction of CO2 to produce higher alcohols, Sustainable Energy & Fuels 2(11) (2018) 2532-2541.
M.H. Yap, K.L. Fow, G.Z. Chen, Synthesis and applications of MOF-derived porous nanostructures, Green Energy & Environment 2(3) (2017) 218-245.
R. Senthil Kumar, S. Senthil Kumar, M. Anbu Kulandainathan, Highly selective electrochemical reduction of carbon dioxide using Cu based metal organic framework as an electrocatalyst, Electrochemistry Communications 25 (2012) 70-73.
K. Zhao, Y. Liu, X. Quan, S. Chen, H. Yu, CO2 Electroreduction at Low Overpotential on Oxide-Derived Cu/Carbons Fabricated from Metal Organic Framework, ACS Applied Materials & Interfaces 9(6) (2017) 5302-5311.
I. Luz, M. Soukri, M. Lail, Confining Metal—Organic Framework Nanocrystals within Mesoporous Materials: a General Approach via "Solid-State" Synthesis, Chemistry of Materials 29(22) (2017) 9628-9638.
R. Kortlever, J. Shen, K.J.P. Schouten, F. Calle-Vallejo, M.T.M. Koper, Catalysts and Reaction Pathways for the Electrochemical Reduction of Carbon Dioxide, the Journal of Physical Chemistry Letters 6(20) (2015) 4073-4082.
H. Li, Y. Li, M.T.M. Koper, F. Calle-Vallejo, Bond-Making and Breaking between Carbon, Nitrogen, and Oxygen in Electrocatalysis, Journal of the American Chemical Society 136(44) (2014) 15694-15701.

(56) References Cited

OTHER PUBLICATIONS

A.A. Peterson, J.K. Narskov, Activity Descriptors for CO2 Electroreduction to Methane on Transition-Metal Catalysts, the Journal of Physical Chemistry Letters 3(2) (2012) 251-258.

S.A. Francis, J.M. Velazquez, I.M. Ferrer, D.A. Torelli, D. Guevarra, M.T. McDowell, K. Sun, X. Zhou, F.H. Saadi, J. John, M.H. Richter, F.P. Hyler, K.M. Papadantonakis, B.S. Brunschwig, N.S. Lewis, Reduction of Aqueous CO2 to 1-Propanol at MoS2 Electrodes, Chemistry of Materials 30(15) (2018) 4902-4908.

Y. Hori, A. Murata, R. Takahashi, S. Suzuki, Enhanced formation of ethylene and alcohols at ambient temperature and pressure in electrochemical reduction of carbon dioxide at a copper electrode. J. Chem. Soc., Chem.Commun. (1988) 17.

H. Noda, S. Ikeda, Y. Oda, K. Ito, Electrochemical reduction of carbon dioxide at various metal electrodes in aqueous potassium hydrogen carbonate solution. Chem. Lett. (1989) 289.

I. Takahashi, O. Koga, N. Hoshi, Y. Hori, Selective Formation of C2 Compounds from Electrochemical Reduction of CO2 at a Series of Copper Single Crystal Electrodes J. Electroanal. Chem. 533 (2002) 135.

Y. Hori, I. Takahashi, O. Koga, N. Electrochemical reduction of carbon dioxide at various series of copper single crystal electrodes. J. Mol. Catal. A 199 (2003) 39.

\* cited by examiner

METHOD OF PRODUCING ISOPROPANOL FROM ELECTROCHEMICAL REDUCTION OF CARBON DIOXIDE AND RELATED COPPER-BASED ELECTROCATALYSTS

CROSS-REFERENCE TO RELATED APPLICATIONS

This application claims the benefit of U.S. Provisional Patent Application No. 62/804,404, filed on Feb. 12, 2019, the entire contents of which are incorporated herein by reference.

FIELD

The present disclosure describes a carbon dioxide reduction reaction electrocatalyst comprising a pyrolyzed copper-based metal-organic framework (MOF) that produces isopropanol from electrochemical reduction of carbon dioxide. The present disclosure also describes a process for producing isopropanol from electrochemical reduction of carbon dioxide comprising applying a potential in an electrochemical cell in the range of about −2V to about −3V versus a silver chloride electrode.

BACKGROUND

Carbon capture and utilization is a means to address increasing atmospheric concentrations of $CO_2$ augmenting climate change. Electrocatalytic reduction in particular has the potential to generate valuable and marketable products, such as short-chain alcohols such as methanol, ethanol, and propanol.

Several classes of copper-based catalysts have been tried and tested for the electrochemical reduction of $CO_2$. For example, metallic copper functions as an electrocatalyst for the reduction of $CO_2$ to multi-carbon, widely-used, products such as propanol. Schwartz et al. developed and evaluated copper nanocrystals (perovskite-type), copper nanoclusters, nanostructured copper alloys, nonporous copper films, and copper nanoflower (chrysanthemum-like) for the production of hydrocarbons and alcohols, and reported increased copper-based nanostructures with increased Faradaic efficiencies for product conversion. In addition, Loiudice et al. found a direct relationship between structure and property relations among copper nanocrystals of variable size and their behavior as electrocatalysts in the $CO_2$ reduction. Munir et al. discovered that Cu—$Cu_2O$, Cu—$Cu_2O$—ZnO, and Cu—ZnO electrodes prepared via electrodeposition produced C1, C2, and C3 species; the Cu—ZnO electrode produced the highest Faradaic efficiency of liquid products (methanol, formate, n-propanol, and acetone) at 97.4%. Cyclic voltammetry studies found that copper (I) metal-organic framework (MOF-)derived species were very selective for $CO_2$ reduction to hydrocarbons and higher alcohols. Zhao et al. utilized carbonized HKUST-1 (900-1100° C.) as an electrode coating to produce alcohol compounds with total faradaic efficiencies of 45.2-71.2% at −0.1 to −0.7 V versus RHE; in addition, they found that the onset potential for ethanol formation is among the lowest overpotentials observed for the reduction of $CO_2$ to ethanol.

Other research has also shown aqueous electrochemical reduction of $CO_2$ to propanol using copper electrodes: Y. Hori, A. Murata, R. Takahashi, S. Suzuki, J. Chem. Soc., Chem.Commun. (1988) 17; H. Noda, S. Ikeda, Y. Oda, K. Ito, Chem. Lett. (1989) 289; Y. Hori, A. Murata, R. Takahashi, J. Chem. Soc., Faraday Trans. 185 (8) (1989) 2309; I. Takahashi, O. Koga, N. Hoshi, Y. Hori, J. Electroanal. Chem. 533 (2002) 135; Y. Hori, I. Takahashi, O. Koga, N. Hoshi, J. Mol. Catal. A 199 (2003) 39.

Yet, there remains a desire to produce isopropanol from electrochemical reduction of carbon dioxide. Isopropanol is widely used for personal care and pharmaceutical applications. Isopropanols' amphipathic nature also makes these compounds great cleaning solvents for various industries. The global isopropanol market was USD $2.84 billion in 2012 and is projected to reach $4.23 billion by 2018. However, isopropanol is made by petrochemical processes that require thermal energy and fossil-fuel-derived hydrocarbon reactants, and has a positive $CO_2$ footprint. Thus, it would be advantageous to provide novel catalysts for electrochemical reduction of carbon dioxide to produce isopropanol and carbon-negative industrial chemicals through electrochemical reduction powered by renewable energy.

SUMMARY OF THE DISCLOSURE

A first aspect of the invention includes a process for producing isopropanol from electrochemical reduction of carbon dioxide. The process includes providing an electrochemical cell comprising a cathode electrode and an anode electrode. The cathode electrode comprises a copper foil electrocatalyst, or a copper mesh electrocatalyst, or an electrocatalyst comprising pyrolyzed PCN-62. The process also includes supplying carbon dioxide to the cathode electrode, and applying a potential between the anode and the cathode, wherein the potential is in the range of about −2V to about −3V versus a silver chloride electrode and the potential is sufficient to electrochemically reduce carbon dioxide and produce isopropanol.

A second aspect of the invention includes a carbon dioxide reduction reaction electrocatalyst that comprises a pyrolyzed copper-based metal-organic framework (MOF). The electrocatalyst produces isopropanol from electrochemical reduction of carbon dioxide. A third aspect of the invention includes an ink composition comprising the electrocatalyst and a polymer. A fourth aspect of the invention includes a cathode electrode for an electrochemical cell comprising a metal catalyst coated with the ink composition.

A fifth aspect of the invention includes a process for the manufacture of a carbon dioxide reduction reaction catalyst, the method comprising: pyrolyzing a copper-based metal-organic framework (MOF).

BRIEF DESCRIPTION OF THE FIGURES

FIGS. 5A-D are scanning electron microscope (SEM) images of (A) a nickel metallic support surface of an electrode with resolution at 50 μm, and a nickel metallic support surface coated with ink comprising carbonized HKUST-1 800° C. with resolution of 50 μm (B), 20 μm (C), and 10 μm (D).

9A-D are graphs depicting faradaic efficiencies for isopropanol, methane, methanol, carbon monoxide as detected by gas and liquid chromatography for tested electrodes (Ni-HKUST-1 400 C, Ni-HKUST-1 600 C, Cu-HKUST-1 600 C, Ni-PCN62 800 C, Cu-PCN62 600 C, Cu-PCN62 800 C, Ni-PCN62 800 C, Cu Foil, Cu Mesh) compared with electrodes coated with commercial catalysts ($La_{1.8}Sr_{0.2}CuO_4$ and Cu electrode) in 0.1 M $KHCO_3$.

DETAILED DESCRIPTION

Described herein is a carbon dioxide reduction reaction electrocatalyst that comprises a pyrolyzed copper-based metal-organic framework (MOF). Advantageously, it has surprisingly been found that the electrocatalyst produces isopropanol from electrochemical reduction of carbon dioxide with a relatively high selectivity. MOFs are highly crystalline hybrid materials that combine metal ions with rigid organic ligands, and are a class of porous materials.

In an exemplary embodiment, the copper-based MOF precursor is PCN-62. PCN stands for porous coordination network. Like other MOFs of the PCN-6X series, PCN-62, having rht topology, can be described as the packing of three types of polyhedra: cuboctahedra (cubOh), truncated tetrahedra (T-Td), and truncated octahedra (T-Oh), wherein the cubOh are constructed from isophthalate moieties and dicopper paddlewheels. PCN-62 can be purchased from Sigma Aldrich (Millipore Sigma, St. Louis, Mo.) or prepared following literature procedures. For example, PCN-62 can be prepared by dissolving $Cu(NO_3)_2 \cdot 6H_2O$ (30 mg) and H6TPBTM (15 mg) in 2 mL of N,N-dimthylformamide (DMF) in a 4 mL Pyrex vial, adding 0.2 mL of $HNO_3$, and then heating the mixture in an 85° C. oven for 12 hours to yield 15 mg of blue crystals.

In another exemplary embodiment, the copper-based MOF precursor is HKUST-1. HKUST stands for Hong Kong University of Science and Technology; and HKUST-1 is also known as MOF-199, Cu-BTC and Basolite™ C300. HKUST-1 is a blue cubic crystal of copper based ultramicroporous MOF made up of copper nodes with 1,3,5-benzenetricarboxylic acid struts between them. It is prepared by solvothermal method, and also can be purchased from Sigma Aldrich.

Pyrolysis is the heating of a material in the absence of (atmospheric) oxygen. Pyrolysis of the copper-based MOFs produces carbonized or pyrolyzed copper-based MOFs. Moreover, pyrolysis of MOFs incorporates the metal center in the MOFs into a carbon matrix. In an exemplary embodiment, pyrolyzed copper-based MOFs are nanocrystals. Because the pyrolyzed or carbonized copper-based MOF does not maintain the crystallinity of the MOF precursor, a copper-based MOF precursor may be chosen irrespective of the MOF's surface area or cavity size.

In an exemplary embodiment, the copper-based MOF precursor also comprises nitrogen, which helps to stabilize the Cu atoms in the pyrolyzed or carbonized form. For example, the organic linker that connects the binuclear copper centers in the PCN-62 MOF is a tri-symmetric amide, which contains three nitrogen atoms per linker. During pyrolysis, nitrogens are incorporated into the graphene base as it is forming defects. Upon deposition, copper atoms migrate and encounter nitrogen atoms in the matrix, to which they are more strongly complexed, adding stability and enhancing selectivity in the resulting copper-based electrocatalyst.

In an exemplary embodiment, the electrocatalyst comprising a pyrolyzed copper-based MOF produces isopropanol with a faradaic efficiency for isopropanol between 3-30%. In an exemplary embodiment, the ratio of the faradaic efficiency for isopropanol to the faradaic efficiency for other carbon products is between about 0.4 to about 2.7.

Further described herein is an ink composition comprising the electrocatalyst and a polymer. The ink is suitable for use in preparing a cathode catalyst layer. In an exemplary embodiment, the polymer comprises a sulfonated polymer with high proton conductivity. Examples of such polymers include: Nafion™ (available from Chemours Company), Aquivion® (Solvay Specialty Polymers), Flemion™ (Asahi Glass Group) and Aciplex™ (Asahi Kasei Chemicals Corp). In one embodiment, the ink composition comprises the catalyst and a dispersion of a proton-conducting polymer in a suitable solvent, such as water, or a mixture of water and organic solvents such as alcohols.

Further described herein is a cathode electrode for an electrochemical cell comprising a metal catalyst coated with the ink composition. In an exemplary embodiment, the metal catalyst is a metallic support comprising copper or nickel. In an exemplary embodiment, the ink composition is drop coated onto the metal catalyst.

Further described herein is a process for producing isopropanol from electrochemical reduction of carbon dioxide. The process includes providing an electrochemical cell comprising cathode electrode and anode electrode. The cathode electrode comprises a copper-based electrocatalyst. In one embodiment, the copper-based electrocatalyst is a copper foil electrocatalyst, a copper mesh electrocatalyst, an electrocatalyst comprising pyrolyzed PCN-62, or an electrocatalyst comprising pyrolyzed HKUST-1. The process also includes supplying carbon dioxide to the cathode electrode, and applying a potential between the anode and the cathode, wherein the potential is in the range of about −2V to about −3V versus a silver chloride electrode and is sufficient to electrochemically reduce carbon dioxide and produce isopropanol.

The applied potential range herein is non-routine. One skilled in the art generally disfavors applying potentials greater than about −2V due to low efficiency and low selectivity. The electrolysis of water or water splitting is the decomposition of water into hydrogen and oxygen due to the energy supplied by a current. This process is not thermodynamically favorable, and requires a standard potential of 1.23 V. In electrochemical processes that take place in aqueous environments, splitting water is non-ideal as the required potential is usually higher than 1.23 V due to the conditions of the cell (this is coined the overpotential). Also, in many electrolyzer studies, the voltage is often limited to a certain range in order to minimize the number of different reactions that may occur at the electrode interface. However, here, it has surprisingly been found that the process comprising applied potentials greater than about −2V (for example, in the range of about −2V to about −2.5V versus a silver chloride electrode) produces isopropanol from electrochemical reduction of carbon dioxide.

In an exemplary embodiment, the applied potential is in the range of about −2V to about −2.5V versus a silver chloride electrode. In another embodiment, the potential is in the range of about −2.3V to about −2.4V versus a silver chloride electrode. In another embodiment, the step of applying a potential comprises a step-wise decrease in voltage. In one embodiment, the step-wise decrease in voltage is from −2.0V to −2.5V versus a silver chloride electrode in hourly increments of −0.1V.

In some embodiments, isopropanol is selectively produced over other carbon products. In one embodiment, the faradaic efficiency for isopropanol is between 3-30%.

In an exemplary embodiment, the cathode electrode comprises a metallic support comprising copper or nickel. In another embodiment, the current delivered to the cathode electrode is in the range of about 100 mA to about 280 mA. In another embodiment, the unreactive carbon dioxide is continually recycled in the electrochemical cell. In another embodiment, the step of supplying carbon dioxide comprises use of flue gas streams or concentrated carbon dioxide streams.

Further described herein is a process for the manufacture of a carbon dioxide reduction reaction catalyst, the method comprising: pyrolyzing a copper-based MOF. In an exemplary embodiment, the pyrolysis of the copper-based MOF is conducted at a temperature in the range of about 350° C. to about 850° C.; about 400° C. to about 800° C.; or about 500° C. to about 700° C. One skilled in the art can optimize and control the ultimate structure (i.e. particle diameter and metal content) of the pyrolyzed or carbonized copper-based MOF by controlling the pyrolysis temperature. The pyrolysis temperature is sufficient as long as the MOF is completely carbonized.

In another embodiment, a copper-based MOF is provided on an electrically conducting support, such as ceramic, or a carbon material (e.g. particulate carbon blacks, heat-treated or graphitized versions thereof, or nanotubes or nanofibers). The pyrolysis of the MOF material is typically conducted for 1 to 60 minutes, preferably 5 to 30 minutes and most preferably 10 to 20 minutes, such as about 15 minutes. The pyrolysis is preferably conducted under an atmosphere comprising an inert gas, such as argon or dinitrogen, or in the presence of a gas reacting with carbon such as ammonia, hydrogen, or mixtures thereof.

EXAMPLE

Preparation of Electrocatalysts, Ink Compositions, and Coated Electrodes

Figure 1:
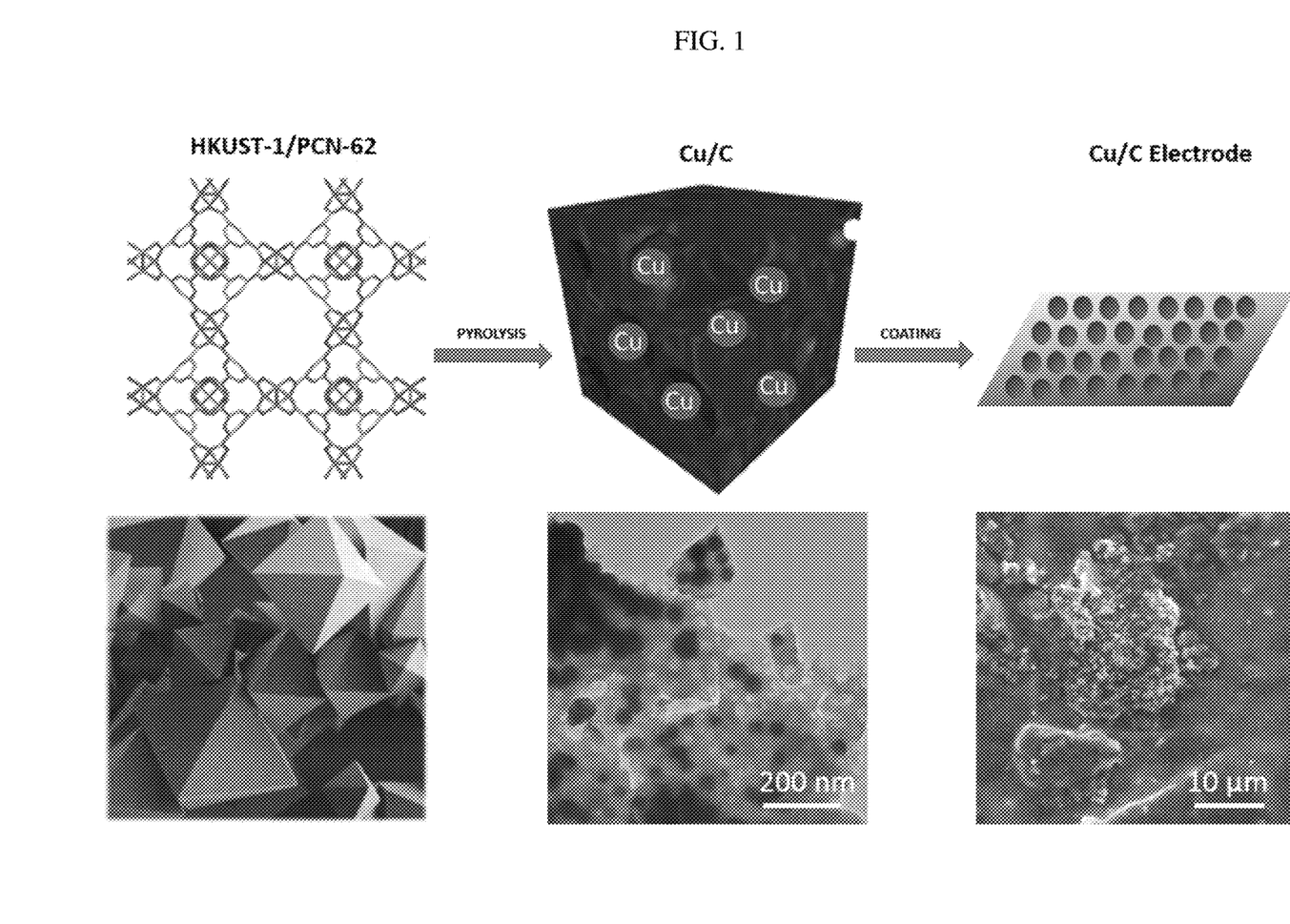
FIG. 1 is an illustrative schematic of the process of preparing the electrodes including pyrolysis of MOF precursors into a metal/carbon powder and coating of metallic support with an ink comprising the carbonized MOF (top row), and corresponding images of the MOF precursor, metal/carbon powder, and electrode ink coating (bottom row).

FIG. 1 is an illustrative schematic of the overall process of preparing the electrodes including pyrolysis of MOF precursors into a metal/carbon powder, and coating of a metallic support with an ink comprising the carbonized MOF (top row). Corresponding images of the MOF precursor, metal/carbon powder, and electrode ink coating are also shown (bottom row).

Pyrolyzed MOFs: Both HKUST-1 and PCN-62 were purchased from Sigma Aldrich (Millipore Sigma, St. Louis, Mo.) or prepared following literature procedures for use as catalyst precursors. Approximately 1 g of the selected MOF was placed in a ceramic boat which was pyrolyzed in a ThermoFisher Scientific Lindberg/Blue M Furnace (ThermoFisher, Waltham, Mass.) at variable temperatures (400-800° C.) under anaerobic conditions. Nitrogen gas purged the furnace at a rate of 10 mL/min. The carbonized powder product was visualized using transmission electron microscopy (TEM) in a JEOL JEM-2000FXS/TEM microscope with LaB6 emitter at 200 kV with a 120 µm condenser lens aperture and 80 µm objective lens aperture inserted. Crystallography of this powder was characterized using X-ray diffraction (XRD) with a D8 Advance Bruker AXS X-ray diffractometer (Billerica, Mass.).

Figure 2:
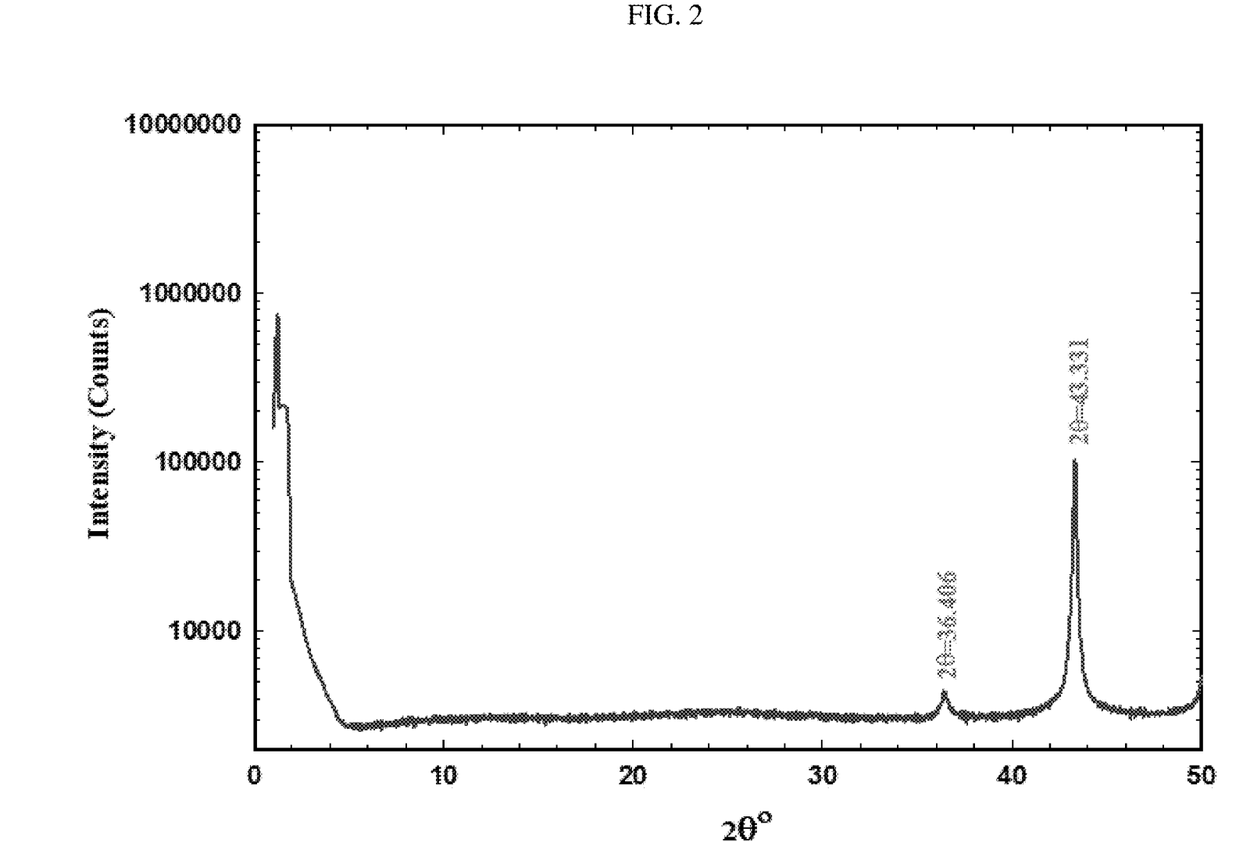
FIG. 2 is a graph showing X-ray diffraction spectra of carbonized PCN-62 600° C. powder.

FIG. 2 is a graph showing X-ray diffraction spectra of carbonized PCN-62 600° C. powder (i.e. carbon-metal powder product of MOF PCN-62 pyrolyzed at 600° C.). As shown in FIG. 2, the pyrolyzed PCN-62 exhibited XRD peaks at $2\theta=36.406$ and 43.311, corresponding to $Cu_2O$ residue and Cu (111), respectively. The intensity counts of XRD evidences minimal $Cu_2O$ compared to Cu, confirming the pyrolysis technique.

Spatial proximity of binuclear copper centers dictated by the large polyaromatic organic linker likely leads to defects on copper nanocrystal faces which are selective for isopropanol over other products.

Figure 3A:
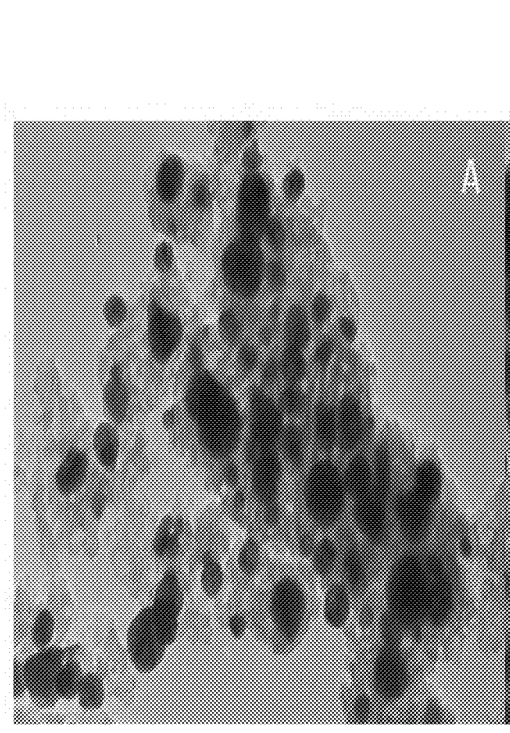
FIGS. 3A-C are transmission electron microscopy (TEM) images of (A) carbonized HKUST-1 600° C. Powder, (B) carbonized HKUST-1 800° C. Powder, and (C) carbonized HKUST-1 800° C. Powder.
Figure 3B:
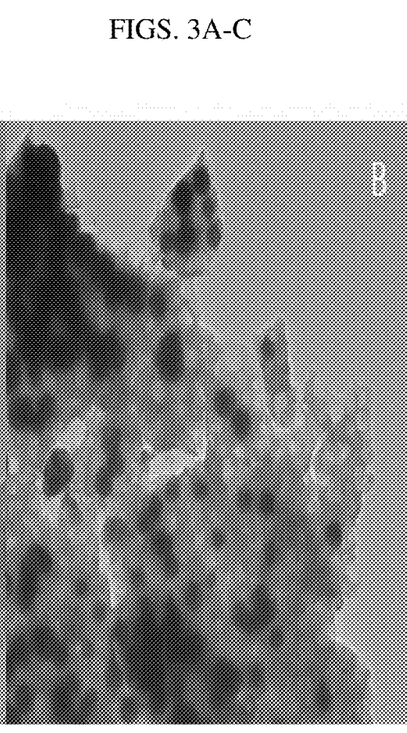
Figure 3C:
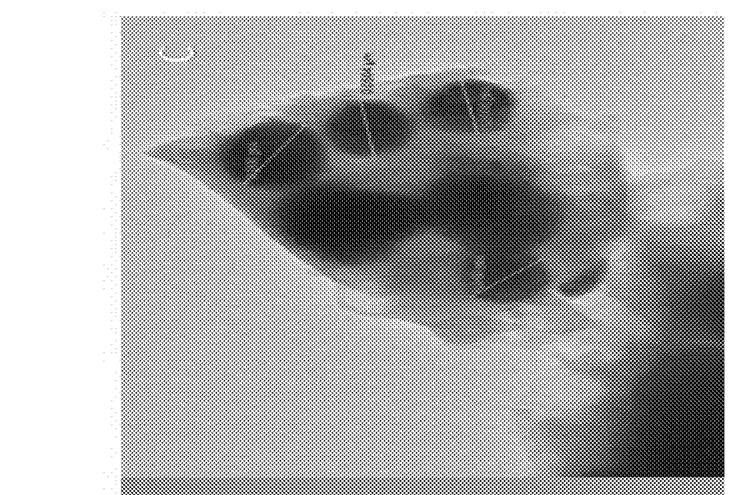

FIGS. 3A-C are transmission electron microscopy (TEM) images of (A) carbonized HKUST-1 600° C. Powder, (B) carbonized HKUST-1 800° C. Powder, and (C) carbonized HKUST-1 800° C. Powder.

Figure 6:
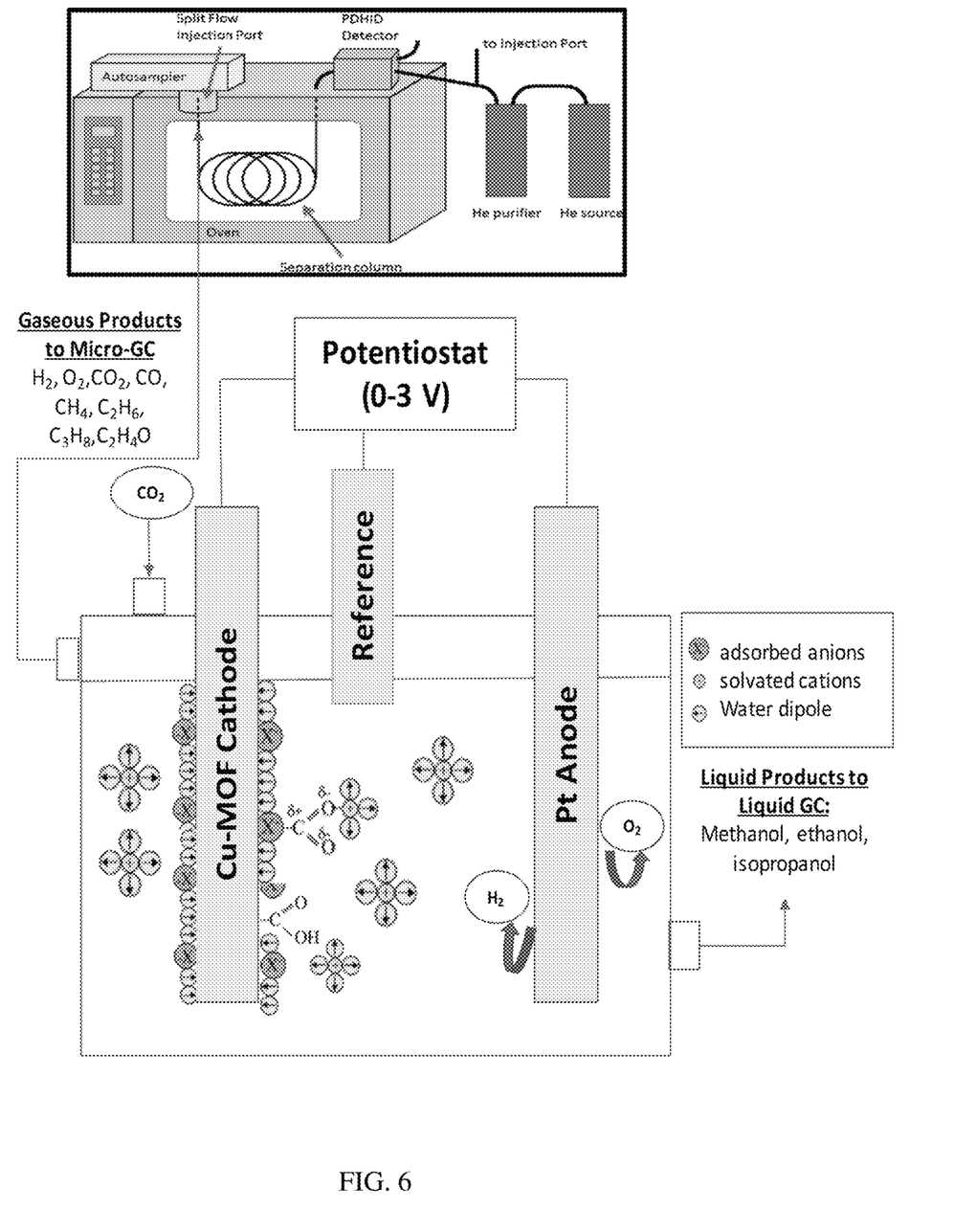
FIG. 6 is an illustrative schematic of the electrochemical set-up with in-situ gaseous analysis and liquid sampling port, and an illustrative diagram of the electrochemical reduction of $CO_2$ at the cathode electrode and water oxidation at the anode electrode.

FIG. 6 shows TEM images of the prepared HKUST-1 powder at both 600 and 800° C.; the catalysts are composed of irregularly spaced copper nanoparticles in a matrix of porous carbon. However, their crystalline structures are different, with the 800° C. ink showing a greater percentage of larger conglomerations of copper-carbon clusters. This polymer matrix is decorated with irregularly spaced copper/carbon clusters from HKUST-1.

Ink Compositions: Roughly 0.2 g of the carbonized powder was placed in a mortar and pestle and was finely grinded into a 20% v/v Naifion in acetone solution. Care was taken to extract the liquid portion of the grinded mix, whilst avoiding the larger solid particles.

Figure 4:
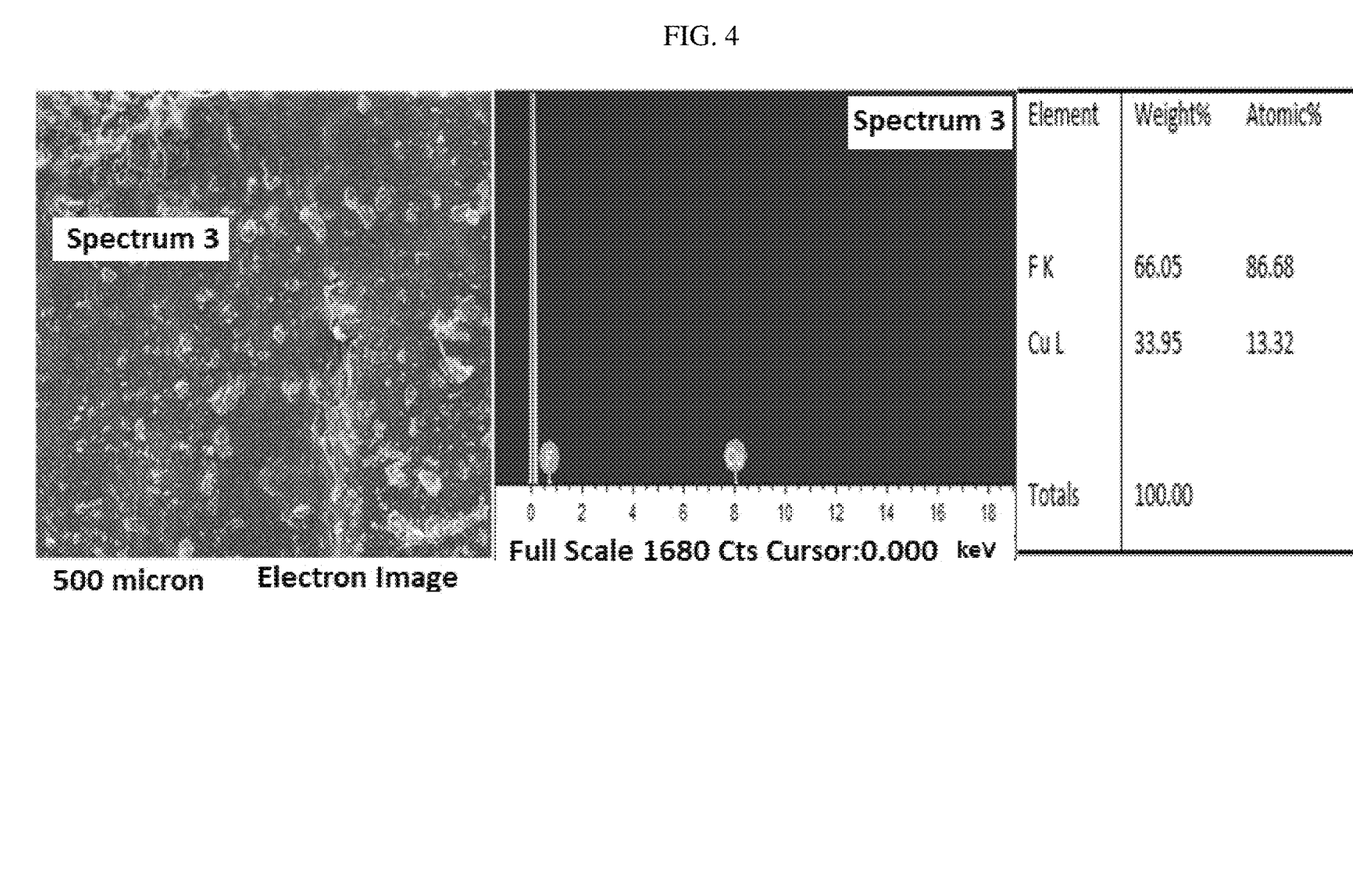
FIG. 4 are Scanning Electron Microscopy with Energy Dispersive Spectroscopy (SEM-EDS images) and data of a cluster embedded in the ink coating comprising carbonized HKUST-1 800 ° C.
Figure 5A:
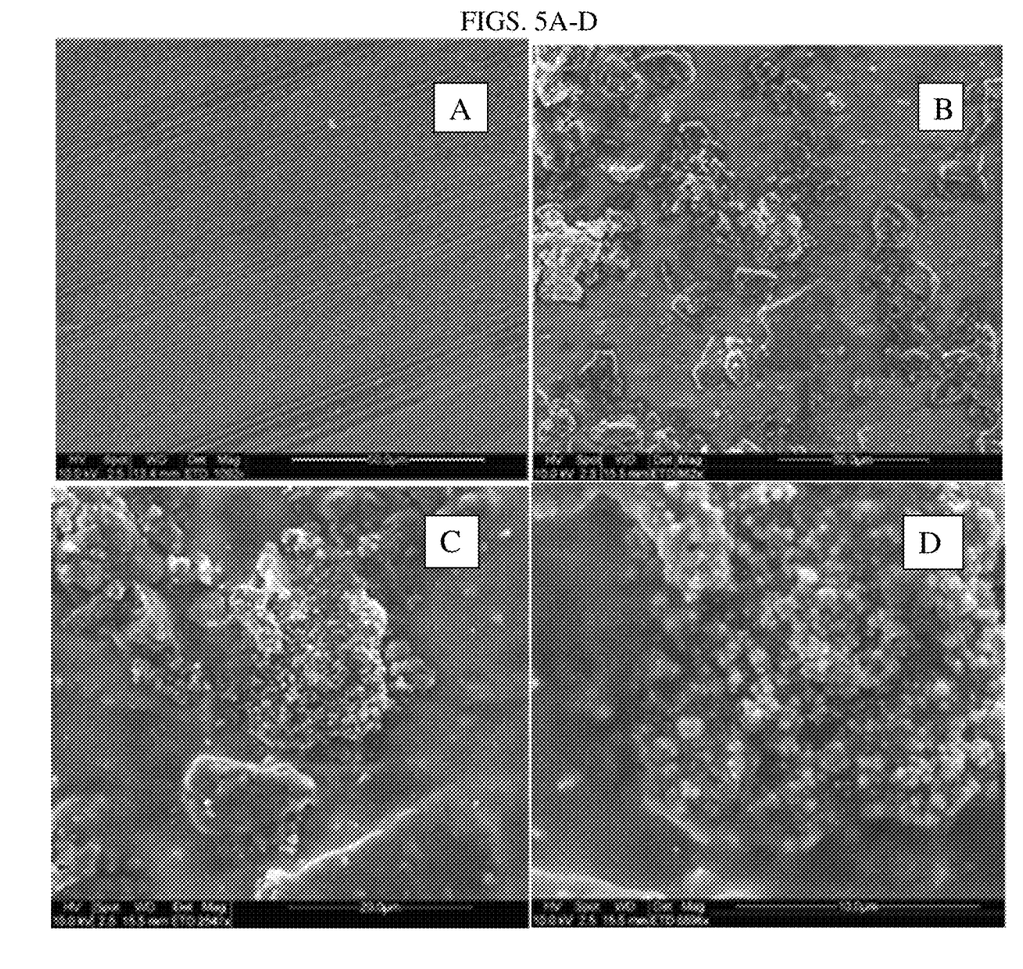

FIG. 4 are SEM-EDS images and data of a cluster embedded in the ink coating comprising carbonized HKUST-1 800° C. The presence of copper in the carbonized matrix is confirmed in the elemental SEM-EDS analysis. Selecting for a small area in a suspected cluster of copper and carbon material revealed a high concentration of copper along with fluorine from the Nafion binder. Carbon was emitted from EDS analysis due to its much higher abundance in the matrix.

Coated Electrodes: Commercially available nickel and copper metallic supports were placed in a Binder Oven (Cole-Parmer, Vernon Hills, Ill.) set at 120° C., and the ink was dropped on the surface of the metallic supports until a thorough coating was observed. These coated electrodes were visualized and elementally characterized using a FEI Quanta 200 scanning electron microscope (SEM) (FEI Company, Hillsboro, Oreg.) in tandem with an Oxford Inca X-sight energy dispersive spectroscopy x-ray detector (EDS) (Oxford Instruments, Abingdon, U.K.).

FIGS. 5A-D are scanning electron microscope (SEM) images of (A) a nickel metallic support surface of an electrode with resolution at 50 μm, and a nickel metallic support surface coated with ink comprising carbonized HKUST-1 800° C. (i.e. ink comprising product of MOF HKUST-1 pyrolyzed at 800° C.) with resolution of 50 μm (B), 20 μm (C), and 10 μm (D). It is evident that Nafion polymer coats the vast majority of the available surface, leaving little, if none, of the original metallic surface available to the reaction interface.

Electrochemical Experimental Set-Up

FIG. 6 is an illustrative schematic of the electrochemical set-up with in-situ gaseous analysis and liquid sampling port, and a diagram of the electrochemical cell depicting the electrochemical reduction of $CO_2$ at the cathode electrode and water oxidation at the anode electrode. A five-port electrochemical cell with a water jacket (Pine Instruments, Durham, N.C.) was used for all experiments. The ports consisted of the following air-tight plugs: one 14/20 PTFE stopper, a 14/20 rubber septum, gas sparging/purging line, a silver chloride reference electrode, and the center port, a 24/25 rubber septum with two holes approximately 1 cm apart that the insulated copper wires connected to both the counter and working electrodes were threaded through. The recirculating water temperature was set at 25° C. A Gamry Reference 3000 Potentiostat (Gamry Instruments, Warminster, Pa.) was used for all electrochemical measurements.

As shown in FIG. 6, at the copper MOF cathode exists a double layer comprised of strongly bound water molecules on the metal surface by electrostatic forces (inner Helmholtz layer) and weakly bound water molecules surrounding anions in solution (outer Helmholtz layer). A direct chemical bond is formed between the metallic surface and the specific adsorption anions. These specifically attracted anions hinder the adsorption of protons and enhances the reduction of CO2 on the surface. Reduced CO2 intermediates interact with both solvated cations through dipole-dipole interactions in the outer Helmholtz layer to form formate radicals as the precursor for the formation of alcohols and hydrocarbons. Due to the applied overpotential, the protons electrochemically reduce on the surface of platinum anode and cause hydrogen evolution along with water splitting. Table 1 below provides expected or known cathode reactions for electrochemical reduction of carbon dioxide, along with standard voltages.

TABLE 1

Standard Redox Potentials for Electrochemical $CO_2$ Conversions

| | ne− | $\Delta G_0$ (kJ/mol) | $E_0$ (Vs. SHE) |
|---|---|---|---|
| Cathode Reactions | | | |
| $CO_2 + 2H^+ + 2e^- \rightarrow CO + H_2O$ | 2 | +19.9 | −0.103 |
| $CO_2 + 8H^+ + 8e^- \rightarrow CH_4 + 2H_2O$ | 8 | −130.8 | +0.169 |
| $CO_2 + 14H^+ + 14e^- \rightarrow C_2H_6 + 4H_2O$ | 14 | −210.8 | +0.156 |
| $CO_2 + 20H^+ + 20e^- \rightarrow C_3H_8 + 6H_2O$ | 20 | −264.3 | +0.137 |
| $2CO_2 + 12H^+ + 12e^- \rightarrow C_2H_4 + 4H_2O$ | 12 | −92 | +0.079 |
| $3CO_2 + 12H^+ + 12e^- \rightarrow C_2H_4O + 4H_2O + CO$ | 12 | −51.7 | +0.045 |
| $CO_2 + 6H^+ + 6e^- \rightarrow CH_3OH + H_2O$ | 6 | −9.1 | +0.016 |
| $2CO_2 + 12H^+ + 12e^- \rightarrow CH_3CH_2OH + 3H_2O$ | 12 | −88.5 | +0.056 |
| $3CO_2 + 18H^+ + 18e^- \rightarrow CH_3CHCH_3OH + 5H_2O$ | 18 | −183 | +0.105 |
| Anode Reaction | | | |
| $6H_2O \rightarrow 3O_2 + 6H_2$ | 12 | −237.14 | 1.234 |

Production of isopropanol has not been previously reported.

Applied Potential: The following is an exemplary process for producing isopropanol from electrochemical reduction of carbon dioxide. The electrochemical cell was filled with 100 mL of 0.05 M $K_2CO_3$ and was purged with $CO_2$ for an hour prior to any voltage application. $CO_2$ was bubbled through continuously at a rate of 25 mL/min throughout the duration of the experiment. Chronoamptometry experiments decreased the voltage from −2.0 to −2.5 in increments of −0.1 V/hour. Just before every voltage change, a syringe was inserted through the rubber septum in order to collect a 1 mL sample in close proximity to the working electrode.

Liquid and Gas Analysis

The headspace gaseous products of the reaction were analyzed using an INFICON 3000 Micro GC (INFICON, Bad Ragaz, Switzerland) with a thermal conductivity detector (TCD) and fast cycling time. The micro GC was calibrated for the detection of hydrogen, oxygen, carbon monoxide, carbon dioxide, methane, ethane, and ethylene oxide. The GC-TCD analyses were split into two methods: method 1 (for % gas molecules using MolSieve 5A PLOT, 10 m×0.32 mm ID column and PLOT U, 3 m×0.32 mm ID pre-column) and method 2 (for ppm gas molecules using PLOT U, 8 m×0.32 mm ID column and PLOT Q, 1 m×0.32 mm ID pre-column), which alternated injections every minute and a half. The purpose of alternating methods was to detect both product hydrocarbon products and side reaction gases. A Hewlett Packard 6890 GC (Hewlett-Packard, Palo Alto, Calif.) with a flame ionization detector (FID) was used for analyzing the alcohol content of the collected liquid samples; the instrument was calibrated for the detection of methanol, ethanol, and isopropanol.

Figure 7A:
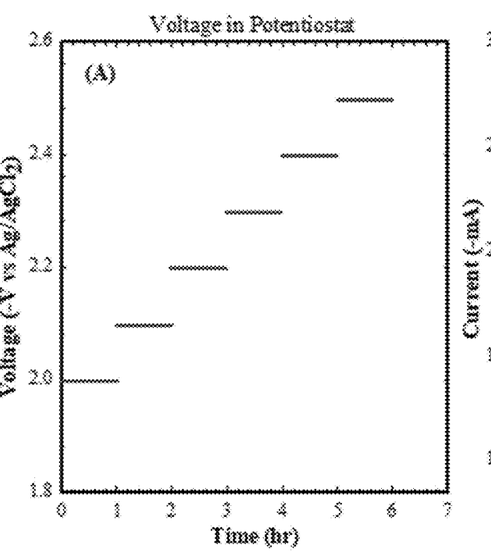
FIG. 7A-D are graphs representing typical experimental potentiostat data with detected gaseous products using Gas Chromatography with Thermal Conductivity Detector (GC-TCD): voltage over time (A), current over time (B), and gaseous products over time (C-D).
Figure 7B:
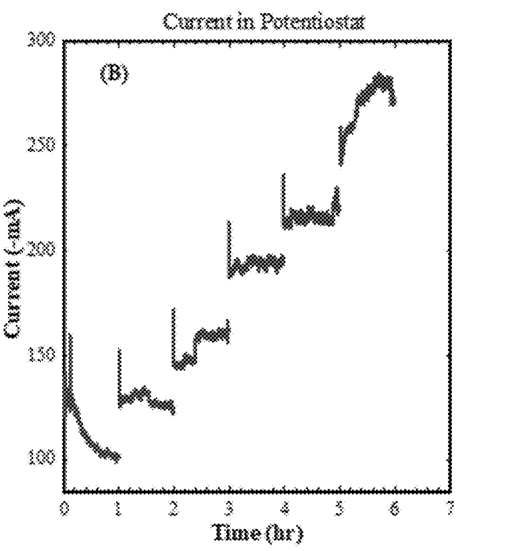
Figure 7C:
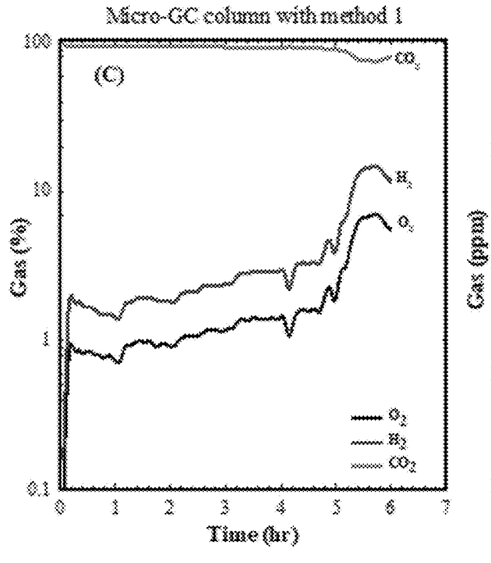
Figure 7D:
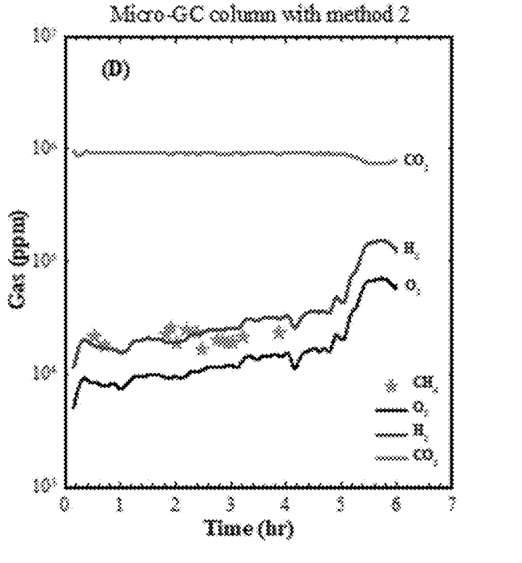

FIG. 7A-D are graphs representing experimental potentiostat and GC-TCD data with detected gaseous products using Gas Chromatography with Thermal Conductivity Detector (GC-TCD): voltage over time (A), current over time (B), and gaseous products over time (C-D). As shown in FIGS. 7A and 7B, the voltage is decreased stepwise from −2.0 V to −2.5 V in −0.1 V increments hourly; subsequently, this increases the amount of current delivered to the working electrode (~100 to 280 mA). As soon as a potential is supplied to the electrode, hydrogen and oxygen are produced via water splitting and the amount of detected $CO_2$ also decreases (~100% to ~93%) due to competing reduction reactions at the working electrode, as shown in FIG. 7C. These side reactions convert $CO_2$ into valuable liquid and gaseous products such as methane, as shown in FIG. 7D.

Figure 8:
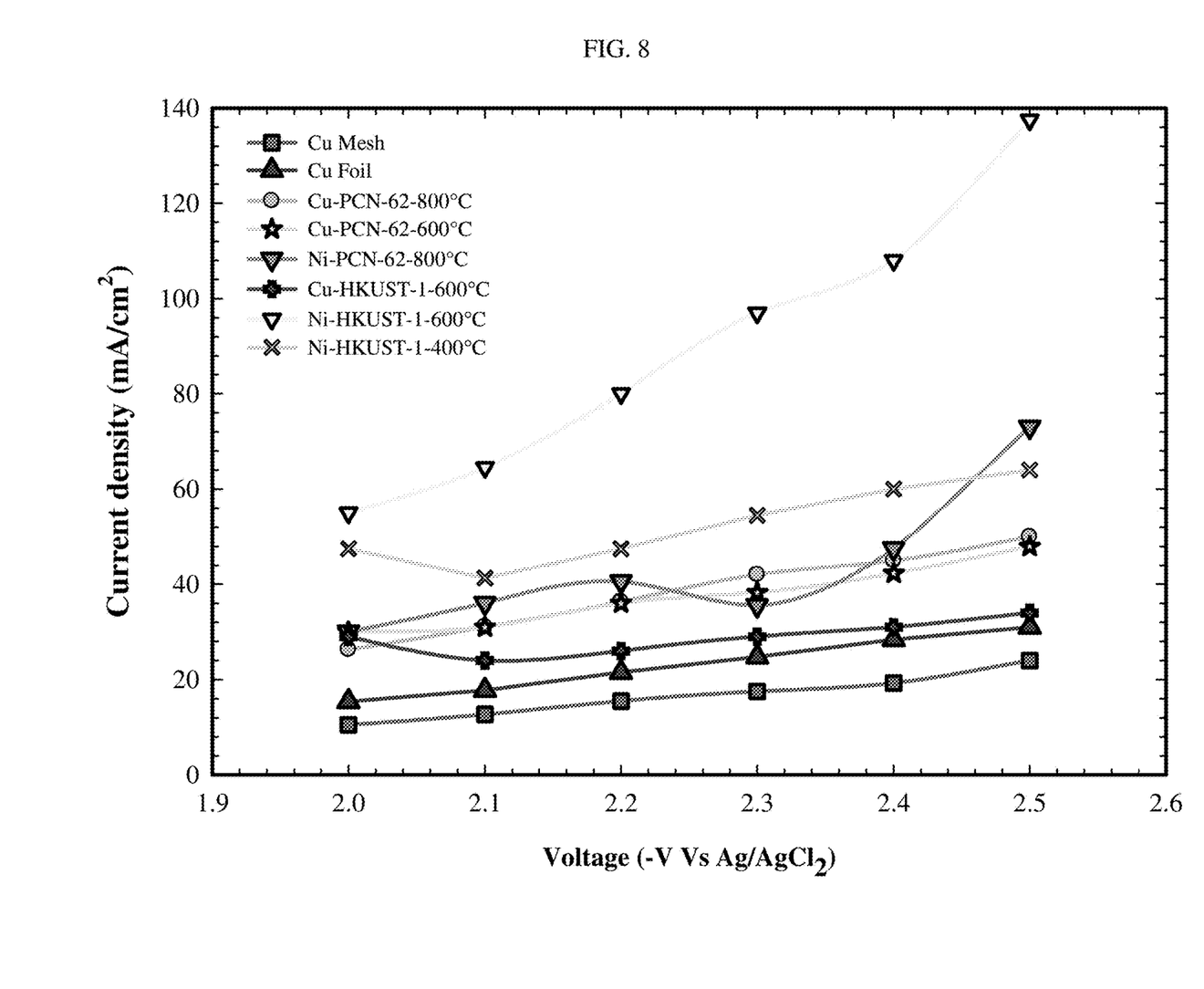
FIG. 8 is a graph depicting current density of tested electrodes at various voltages versus a silver chloride electrode.

FIG. 8 is a graph depicting current density of tested electrodes at various voltages versus a silver chloride electrode. As shown in FIG. 8, it is clear that the addition of a carbonized MOF coating increases the current density of a commercial electrode at differing voltages. Tested nickel-based catalysts were able to achieve higher current densities than that of copper-derived electrodes, on average. This observation is especially evident with HKUST-1 coated onto nickel substrate. In addition, as the pyrolysis temperature increases, there is an increase in current density of a coated electrode. This is explained due to an increase in the carbonized portion of the MOF, subsequently reducing available surface area and acting as a better conductive material.

Figure 9A:
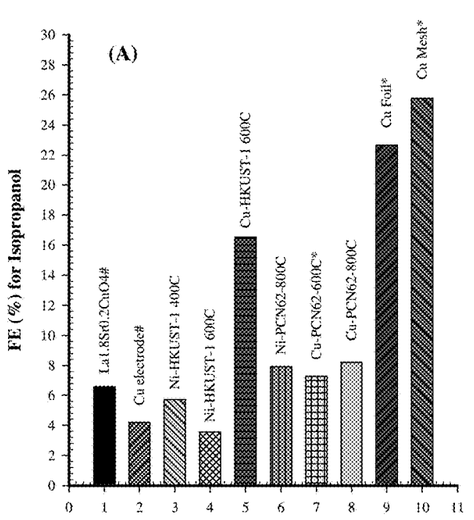

FIG. 9A-D are graphs depicting faradaic efficiencies for isopropanol, methane, methanol, carbon monoxide as detected by gas and liquid chromatography for tested electrodes (Ni-HKUST-1 400C, Ni-HKUST-1 600C, Cu-HKUST-1 600C, Ni-PCN62 800C, Cu-PCN62 600C, Cu-PCN62 800C, Cu Foil, Cu Mesh) compared with electrodes coated with commercial catalysts ($La_{1.8}Sr_{0.2}CuO_4$ and Cu electrode) in 0.1 M $KHCO_3$. As shown in FIG. 9A, Isopropanol Faradaic efficiencies are ranked in the following order: Cu Mesh>Cu Foil>Cu HKUST-1 600° C.>Ni PCN-62 800° C.=Cu PCN-62 800° C.>Cu PCN-62 600° C.>$La_{1.8}Sr_{0.2}CuO_4$>Ni HKUST-1 400° C.>Cu electrode>Ni HKUST-1 600 ° C. It is surprising that the electrochemical reduction of carbon dioxide produced isopropanol.

FIGS. 8 and 9A-D, together, demonstrate is an inverse relationship between the isopropanol Faradaic efficiency and current density for these materials. The cathodically formed alcoholic product can be oxidized at the Pt anode with sufficient current density to form intermediate products such as CO, methanol, formate ion products, and methane, seen in Table 1.

Faradaic efficiencies for $H_2$ evolution reaction (HER), $CO_2$ reduction reactions to different Carbon products over HER, and isopropanol production over other carbon products were determined. Table 2 below summarizes the results of the different electrocatalysts tested.

TABLE 2

The $CO_2$ reduction reaction (CO2RR) catalytic behavior of the studied electrocatalysts

| Electro-Catalyst | $FE_{HER}$ (%)[a] | $FE_{CO2RR}$ (%)[b] | $FE_{isopropanol}/FE_{other}$[c] |
|---|---|---|---|
| Cu Mesh | 56.7 | 43.3 | 1.5 |
| Cu Foil | 62.9 | 37.1 | 1.6 |
| Cu-PCN62 800° C. | 91.8 | 8.2 | 1.9 |
| Cu-PCN62 600° C. | 92.7 | 7.3 | 2 |
| Ni- PCN62 800° C. | 70.9 | 29.1 | 0.4 |
| Cu-HKUST-1 600° C. | 77.5 | 22.5 | 2.7 |
| Ni-HKUST-1 600° C. | 24.9 | 75.1 | 0.1 |
| Ni-HKUST-1 400° C. | 92.1 | 7.9 | 1.9 |

Figure 9B:
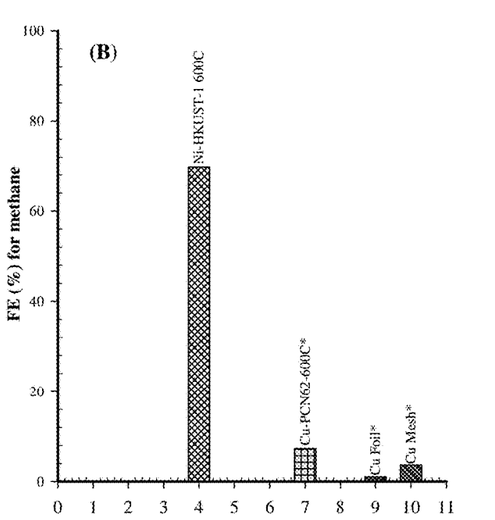
Figure 9C:
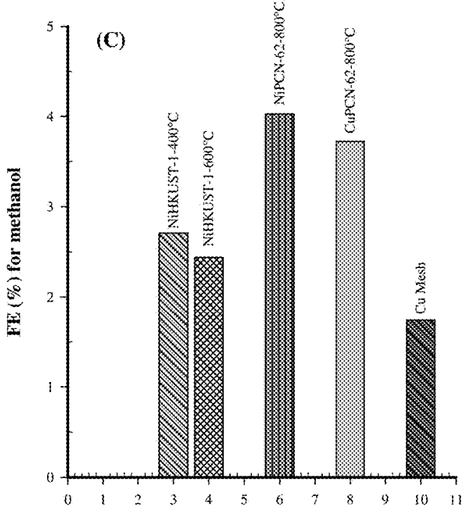
Figure 9D:
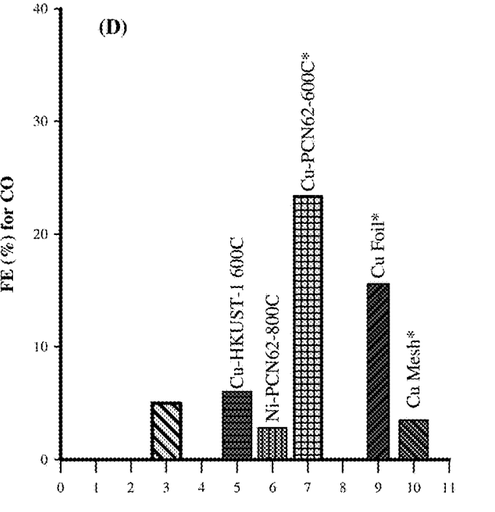

[a]Faradaic efficiency for $H_2$ evolution reaction;
[b]Faradaic efficiency for $CO_2$ reduction reactions to different Carbon products;
[c]$FE_{isopropanol}/FE_{other}$ = Selectivity of isopropanol production over other C-products
Ni-HKUST-1 600° C. showed the highest faradaic efficiency over HER with major product as methane as shown in FIG. 9B, whereas Cu-PCN62 600° C. produced lower faradaic efficiency over HER with major product as CO as shown in FIG 9C. Selectivity of Cu-HKUST-1 600° C. found to be highest (2.7) with major product as isopropanol as shown in FIG. 9A with faradaic efficiency of 22.5%, followed by Cu-PCN62 600° C. with faradaic efficiency of 8.2% and major product as methanol as shown FIG. 9C.

TABLE 3

Comparison of isopropanol formation with the production of propanol from literature at different experimental conditions

| | Experimental conditions | Current density | Faradic efficiency for propanol |
|---|---|---|---|

TABLE 3-continued

Comparison of isopropanol formation with the production of propanol from literature at different experimental conditions

| Catalysts | (V vs $Ag/AgCl_2$) | (mA/cm$^2$) | (%) |
|---|---|---|---|
| Cu nanocrystals-10[29] | −1.15 V | 1.74 | 8.8 |
| Cu nanocrystals-20[29] | −1.05 V | 1.5 | 10.6 |
| Electropolished Cu[10] | −1.2 V | 0.2 | 4 |

| Catalysts | Experimental conditions (V vs $Ag/AgCl_2$) | Current density (mA/cm$^2$) | Faradic efficiency for isopropanol (%) |
|---|---|---|---|
| Cu Mesh | −2 to −2.4 V | 10.5-24 | 10-25.8 |
| Cu Foil | −2 to −2.4 V | 15.38-31 | 14.5-24 |
| Cu-PCN62 800° C. | −2 to −2.4 V | 26.25-50 | 5.8-8.2 |
| Cu-PCN62 600° C. | −2 to −2.4 V | 30-48 | 5.9-7.3 |
| Ni- PCN62 800° C. | −2 to −2.4 V | 30-73 | 4.2-7.9 |
| Cu-HKUST-1 600° C. | −2 to −2.4 V | 29-34 | 9.8-16.5 |
| Ni-HKUST-1 600° C. | −2 to −2.4 V | 55-137.5 | 2.1-3.6 |
| Ni-HKUST-1 400° C. | −2 to −2.4 V | 47.5-64 | 4.9-5.7 |

Figure 10:
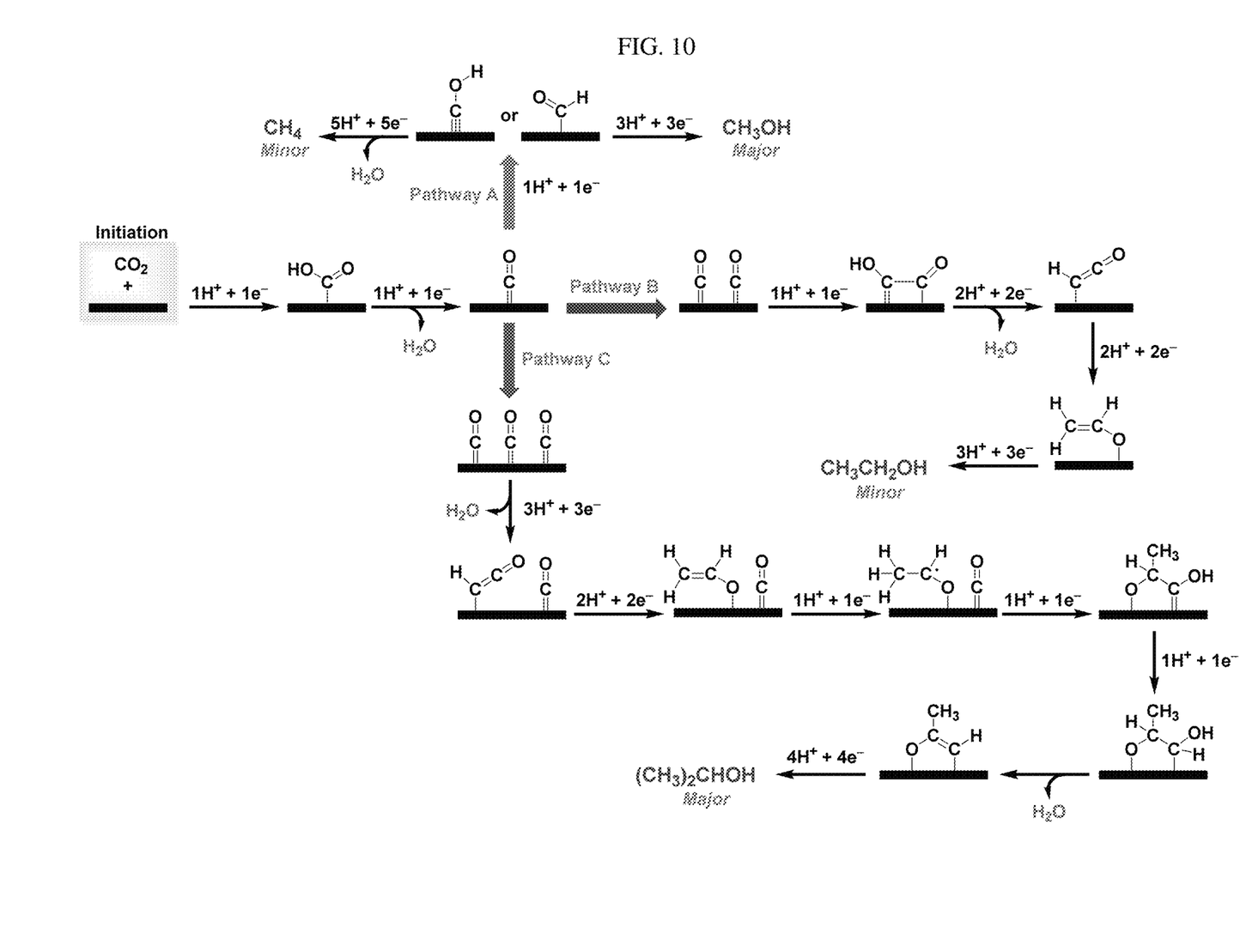
FIG. 10 illustrates possible reaction pathways for $CO_2$ electrochemical reduction with copper-based electrocatalysts, forming isopropanol (($CH_3)_2CHOH$), ethanol ($CH_3CH_2OH$), methanol ($CH_3OH$), and methane ($CH_4$)

FIG. 10 illustrates possible reaction pathways for $CO_2$ electrochemical reduction with the tested catalysts, forming isopropanol (($CH_3)_2CHOH$), ethanol ($CH_3CH_2OH$), methanol ($CH_3OH$), and methane ($CH_4$). Based on the experimental results and extensive mechanistic studies conducted by Kopar and coworkers, possible electrochemical reduction pathways of $CO_2$ to produce methane and alcohols are shown in FIG. 10. The reduction initiates with a proton-electron transfer binding $CO_2$ to the surface as a $*CO_2H$ species. A subsequent proton-electron reduction followed by the release of water forms the key intermediate *CO. Formation of $C_1$ products results from the reduction of the *CO intermediate via proton-electron transfer to produce formyl *CHO and hydroxymethylidyne *COH species (FIG. 10, Pathway A). At high current densities, 60-140 mA/cm$^2$ at −2.0 to −2.5 V, displayed with the Ni-HKUST-1 600° C. catalyst, the *CO species are reduced rapidly to yield methane, while lower current densities, 30-60 mA/cm$^2$ from −2.0to −2.5 V, can lead to methanol, as observed for the Ni-PCN-62 800° C. catalyst. The oxidation of methanol to formate may also occur, however, went undetected by our GC method. The formation of $C_2$ products arises from the dimerization of reduced *CO species via an initial electron transfer forming a C—C bond followed by a proton transfer to give a $*C_2O_2H$ dimer (FIG. 10, Pathway B). The $*C_2O_2H$ dimer formation is purported to arise from a square arrangement of the *CO species. Rearrangement and reduction of the oxygenated enol $*C_2H_3O$ species results in ethanol production, which was only observed for the Ni-PCN-62 catalyst. At low current densities, reductive *CO dimerization occurs to give the enol $*C_2H_3O$ (FIG. 10, Pathway C). A high surface density of *CO on the catalyst at lower energies may allow for the formation of a new C—C bond from the radical coupling of $*C_2H_3O$ with a neighboring *CO. Additional proton-electron transfers and release of water can form a $C_3$ enol species that follows the reductive pathway of ethanol to produce isopropanol. The highest selectivity for isopropanol was observed with the Ni-PCN-62 catalyst. Nickel electrodes have been shown to bind CO strongly, which may account for $C_3$ products. The low production of ethanol may stem from ethanol being consumed at the electrode to give isopropanol. Recently, $MoS_2$ electrodes were found to produce t-butanol ($C_4$ product) at very low current densities. The $C_4$ product t-butanol could arise similarly through the mechanism proposed in this work.

Numerous modifications and variations of the present disclosure are possible in view of the above teachings. It is understood that within the scope of the appended claims, the disclosure may be practiced otherwise than as specifically described herein.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

The invention claimed is:

1. A method of producing isopropanol from electrochemical reduction of carbon dioxide comprising:
providing an electrochemical cell comprising a cathode electrode and an anode electrode, wherein the cathode electrode comprises a copper-based metal organic framework (MOF), wherein the copper-based MOF is pyrolyzed, wherein the copper-based MOF is coated on a nickel support surface;
supplying carbon dioxide to the cathode electrode; and
applying a potential between the anode and the cathode, wherein the potential is in a range of about −2V to about −3V versus a silver chloride electrode and is sufficient to electrochemically reduce the carbon dioxide and produce isopropanol.

2. The method of claim 1, wherein the copper-based MOF comprises PCN-62 or HKUST-1.

3. The method of claim 1, wherein applying the potential in the range of about −2V to about −3V comprises decreasing step-wise in hourly increments of −0.1V.

4. The method of claim 1, wherein a current delivered to the cathode electrode is in a range of about 100mA to about 280mA.

5. The method of claim 1, wherein unreacted carbon dioxide is continually recycled in the electrochemical cell.

6. The method of claim 1, wherein the copper-based MOF produces the isopropanol with a faradaic efficiency in a range of about 3% to about 30%.

7. The method of claim 1, wherein the step of supplying carbon dioxide comprises use of flue gas streams or concentrated carbon dioxide streams.

8. The method according to claim 1, wherein the copper-based MOF further comprises nitrogen.

9. The method of claim 1, wherein the copper-based MOF produces the isopropanol with a ratio of faradaic efficiency for isopropanol to faradaic efficiency for other carbon products in the range of about 0.4 to about 2.

10. A method of producing isopropanol from electrochemical reduction of carbon dioxide comprising:
providing an electrochemical cell comprising a cathode electrode and an anode electrode, wherein the cathode electrode comprises a copper-based metal organic framework (MOF), wherein the copper-based MOF is pyrolyzed;
supplying carbon dioxide to the cathode electrode; and
applying a potential between the anode and the cathode, wherein the potential is in a range of about −2V to about −3V versus a silver chloride electrode, wherein a current delivered to the cathode electrode is in a range of about 100mA to about 280mA, and wherein the potential is sufficient to electrochemically reduce the carbon dioxide and produce isopropanol.

11. The method of claim 10, wherein the copper-based MOF comprises PCN-62or HKUST-1.

12. The method of claim 10, wherein applying the potential in the range of about −2V to about −3V comprises decreasing step-wise in hourly increments of −0.1V.

13. The method of claim 10, wherein unreacted carbon dioxide is continually recycled in the electrochemical cell.

14. The method of claim 10, wherein the copper-based MOF produces the isopropanol with a faradaic efficiency in a range of about 3% to about 30%.

15. The method of claim 10, wherein the step of supplying carbon dioxide comprises use of flue gas streams or concentrated carbon dioxide streams.

16. The method of claim 10, wherein the copper-based MOF produces the isopropanol with a faradaic efficiency in the range of about 5% to about 20%.

17. The method of claim 10, wherein the potential is in a range of about −2.3V to about −2.4V versus the silver chloride electrode.

18. The method of claim 10, wherein the copper-based MOF further comprises nitrogen.

19. The method of claim 10, wherein the copper-based MOF produces the isopropanol with a ratio of faradaic efficiency for isopropanol to faradaic efficiency for other carbon products in the range of about 0.4 to about 2.

* * * * *